(12) United States Patent
Li et al.

(10) Patent No.: US 9,221,857 B2
(45) Date of Patent: Dec. 29, 2015

(54) PYRIDINE-OXYPHENYL COORDINATED IRIDIUM (III) COMPLEXES AND METHODS OF MAKING AND USING

(75) Inventors: Jian Li, Phoenix, AZ (US); Eric Turner, Chandler, AZ (US); Nathan J. Bakken, Scottsdale, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 471 days.

(21) Appl. No.: 13/446,354

(22) Filed: Apr. 13, 2012

(65) Prior Publication Data
US 2012/0264938 A1   Oct. 18, 2012

Related U.S. Application Data

(60) Provisional application No. 61/475,321, filed on Apr. 14, 2011.

(51) Int. Cl.
*C07F 15/00* (2006.01)
*H01L 51/50* (2006.01)

(52) U.S. Cl.
CPC .................................. *C07F 15/0033* (2013.01)

(58) Field of Classification Search
USPC .............................................. 546/2; 313/504
See application file for complete search history.

(56) References Cited

U.S. PATENT DOCUMENTS

| | | | | |
|---|---|---|---|---|
| 7,064,228 B1 * | 6/2006 | Yu et al. | ........................ | 556/489 |
| 2001/0019782 A1 | 9/2001 | Igarashi et al. | | |
| 2004/0230061 A1 | 11/2004 | Seo et al. | | |
| 2006/0024522 A1 | 2/2006 | Thompson | | |
| 2006/0127696 A1 | 6/2006 | Stossel | ........................ | 428/690 |
| 2006/0182992 A1 | 8/2006 | Nii | ................................ | 546/4 |
| 2006/0255721 A1 | 11/2006 | Igarashi | ........................ | 428/690 |
| 2010/0141127 A1 | 6/2010 | Xia et al. | | |

FOREIGN PATENT DOCUMENTS

| | | |
|---|---|---|
| JP | 2002105055 A | 4/2002 |
| JP | 2003342284 A | 12/2003 |
| JP | 2007031678 A | 2/2007 |
| JP | 2009076509 A | 4/2009 |
| TW | 101113338 | 10/2012 |
| WO | WO 00/70655 | 11/2000 |
| WO | WO2004085450 A2 | 10/2004 |
| WO | WO2006067074 A1 | 6/2006 |
| WO | WO2005113704 A3 | 8/2006 |
| WO | WO2006115301 A1 | 11/2006 |
| WO | WO 2010/007098 | 1/2010 |
| WO | WO2010056669 A1 | 5/2010 |
| WO | WO 2010/093176 | 8/2010 |
| WO | WO 2012/142387 | 10/2012 |

OTHER PUBLICATIONS

International Search Report issued Jul. 2, 2012 by the International Searching Authority for application PCT/US2012/033484 filed on Apr. 13, 2012 (Applicant—Arizona Board of Regents//1st Named Inventor—Li) (3 pages).

Rui Zhu et al., "Color tuning based on a six-membered chelated iridium (III) complex with aza-aromatic ligand," Chemistry Letters, vol. 34, No. 12, 2005, pp. 1668-1669.

Office Action and Search Report (including English translation) for Taiwan Patent Application No. 101113338, issued Sep. 7, 2015, 7 pages.

* cited by examiner

*Primary Examiner* — Charanjit Aulakh
(74) *Attorney, Agent, or Firm* — Fish & Richardson P.C.

(57) ABSTRACT

Iridium (III) complexes are described together with methods to prepare and use such complexes. Also described are devices that utilize the iridium (III) complexes.

17 Claims, 2 Drawing Sheets

PYRIDINE-OXYPHENYL COORDINATED IRIDIUM (III) COMPLEXES AND METHODS OF MAKING AND USING

CROSS REFERENCE TO RELATED APPLICATIONS

This application claims priority to U.S. Provisional Patent Application No. 61/475,321, filed on Apr. 14, 2011, which is hereby incorporated by reference in its entirety.

BACKGROUND

1. Technical Field

The present disclosure relates to iridium complexes which are capable of absorbing and/or emitting light and are thus useful as an emissive or absorption material in a device.

2. Technical Background

Compounds capable of absorbing and/or emitting light are ideally suited for use in a wide variety of applications, including optical and electro-optical devices, photo-absorbing devices, and as markers for bio-applications. Much research has been devoted to the discovery and optimization of organic and organometallic materials for use in such applications. Generally, research in this area aims to accomplish a number of goals, including improvements in absorption and emission efficiency, as well as improvements in processing ability, among others.

Despite significant advances in research devoted to optical, electro-optical, and marker materials, existing materials have a number disadvantages, including poor processing ability, inefficient emission or absorption, and less than ideal stability, among others. Thus, a need exists for new materials which exhibit improved performance in optical emitting and absorbing applications. This need and other needs are satisfied by the present invention.

SUMMARY

The present invention relates to iridium complexes that exhibit photoabsorption and photoemission, to methods of making such compounds, and to applications thereof, including optical devices comprising the compounds.

In one aspect, the present invention provides a tetradentate iridium (III) complex represented by the formula:

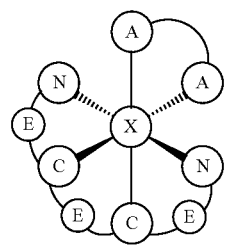

wherein X represents an iridium atom, each C represents a carbon moiety, each N represents a nitrogen moiety, each E represents an optional bridging atom, such as, for example, carbon or oxygen, and each A represents an ancillary ligand that can be used to balance the charge on the complex.

In another aspect, the present invention provides a tetradentate iridium (III) complex represented by the formula:

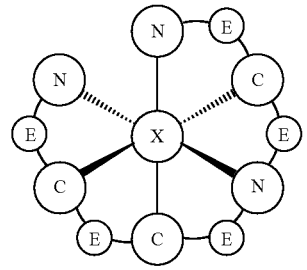

wherein X represents an iridium atom, each C represents a carbon moiety, each N represents a nitrogen moiety, each E represents an optional bridging atom, such as, for example, carbon or oxygen.

In another aspect, the present invention provides a hexadentate indium (III) complex represented by the formula:

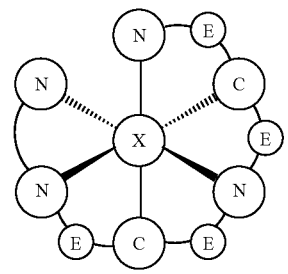

wherein X represents an iridium atom, each C represents a carbon moiety, each N represents a nitrogen moiety, each E represents an optional bridging atom, such as, for example, carbon or oxygen.

In another aspect, the present invention provides a tetradentate hexadentate iridium (III) complex represented by the formula:

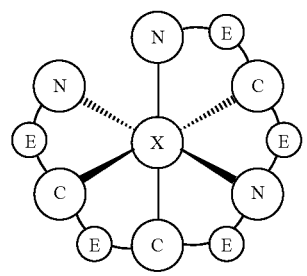

wherein X represents an iridium atom, each C represents a carbon moiety, each N represents a nitrogen moiety, each E represents an optional bridging atom, such as, for example, carbon or oxygen.

In still another aspect, the present invention provides a hexadentate iridium (III) complex represented by the formula:

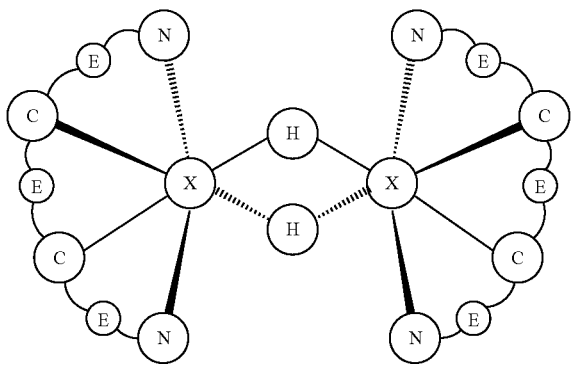

wherein X represents an iridium atom, each C represents a carbon moiety, each N represents a nitrogen moiety, each E represents an optional bridging atom, such as, for example, carbon or oxygen, and each H represent a bridging atom, such as, for example, a halogen, such as a chloride.

In yet another aspect, the present invention provides an organic photovoltaic device comprising, as a donor or acceptor material, one or more of the iridium (III) complexes described herein.

In yet another aspect, the present invention provides a luminescent bio-marker comprising one or more of the iridium (III) complexes described herein.

Also disclosed are optical devices, such as organic light emitting devices, photovoltaic devices (e.g., solar cells), and luminescent display devices that comprise one or more compounds of the invention as a functional material, such as a light-emitter or absorber, or both.

BRIEF DESCRIPTION OF THE FIGURES

The accompanying figures, which are incorporated in and constitute a part of this specification, illustrate several aspects and together with the description serve to explain the principles of the invention.

Figure 1:
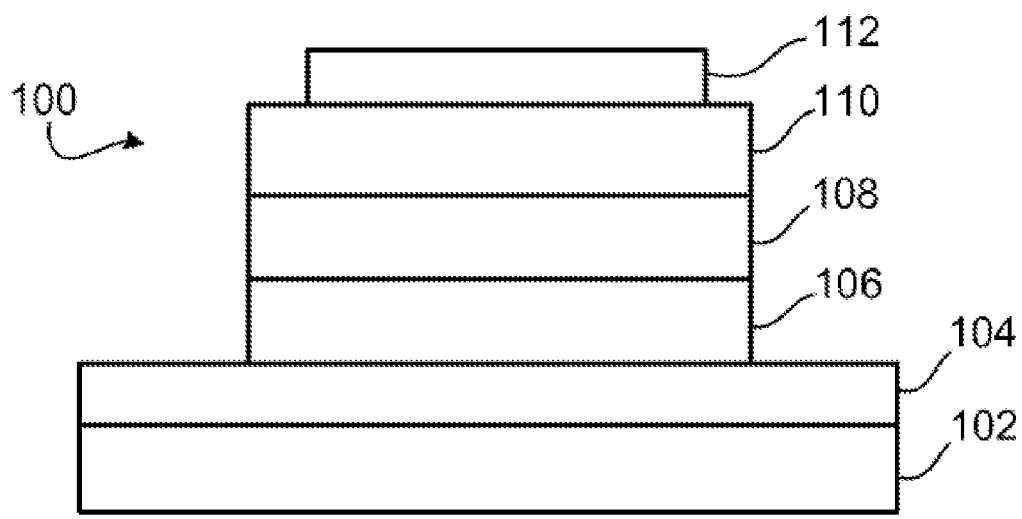
FIG. 1 is a drawing of a cross-section of an exemplary organic light-emitting diode (OLED).

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As briefly described above, the present invention is directed to iridium complexes, such as, for example, iridium (III) complexes. In one aspect, the invention comprises a tetradentate iridium (III) complex. In another aspect, the invention comprises a hexadentate iridium (III) complex. In yet another aspect, the emission energy of an inventive iridium complex can be adjusted by modifying one or more of the ligands coordinated to the iridium metal center. In another aspect, the invention comprises an iridium atom coordinated with one or more tetradentate ligands, hexadentate ligands, or a combination thereof.

As used herein, references to "C", "E", "A", and "N" are intended to refer to moieties or functions groups on the described complex. In one aspect, reference to a "C" or an "N" can refer to a moiety comprising such an atom, for example, a carbon or nitrogen, respectively. In another aspect, reference to a "C" or an "N" can refer to a moiety as described herein The inventive iridium complexes of the present disclosure can, in various aspects, exhibit phosphorescent properties. In another aspect, the emission spectrum of an iridium complex can be tuned, for example, so as to provide a desired color for a particular application. In such an aspect, the emission spectrum can be tuned, for example, from the ultraviolet to the near infrared by modifying the ligand structure of the complex.

As used herein, references to "C", "E", "A", and "N" are intended to refer to moieties or functions groups on the described complex. In one aspect, reference to a "C" or an "N" can refer to a moiety comprising such an atom, for example, a carbon or nitrogen, respectively. In another aspect, reference to a "C" or an "N" can refer to a moiety as described herein.

In one aspect, each C represents a moiety comprising 1-10 carbon atoms. For example, the moiety can comprise 6 carbon atoms. In another aspect, the carbon atoms can form a ring structure, such as an aromatic ring structure. Suitable moieties include, but are not limited to, substituted and unsubstituted aryl or cycloalkyl, preferably substituted and unsubstituted aryl. In one aspect, the aryl can be substituted and unsubstituted phenyl. In another aspect, the aryl can be unsubstituted phenyl. Unsubstituted phenyl refers to a structure that is not substituted except for the linkages to other moieties as show in the formulas disclosed herein. For example, a phenyl without further substitutions bonded to X, C and N as shown in the formulas described herein is an unsubstituted aryl or phenyl. Substituted aryl, for example, refers to an aryl group that can be substituted with one or more groups including, but not limited to, optionally substituted alkyl, cycloalkyl, alkoxy, amino, ether, halide, hydroxy, nitro, silyl, sulfo-oxo, or thiol, as described herein. In other aspects, C can represent other moieties not specifically recited herein, but that are described in any of the structures, figures, or examples provided herein, or that one of skill in the art would contemplate as a variant, analog, and/or suitable structure for an intended application In one aspect, N represents a moiety comprising 1-10 atoms, wherein in at least one atom is nitrogen and the remaining atoms are either carbon, nitrogen, oxygen or sulfur atoms. For example, the moiety can comprise one nitrogen atom and three, four or five carbon atoms. In anther example, the moiety can comprise two nitrogen atoms and two, three or four carbon atoms. The moiety can be a ring structure. In one aspect, the ring structure is aromatic. In another aspect, the ring structure is not aromatic. The ring structures can be substituted or unsubstituted. Substituted N moieties include substitutions with one or more groups including, but not limited to, optionally substituted alkyl, cycloalkyl, alkoxy, amino, ether, halide, hydroxy, nitro, silyl, sulfo-oxo, or thiol, as described herein. In one aspect, one or two carbon atoms in the N moiety can be substituted with an alkyl group. Suitable N moieties include, but are not limited to substituted and unsubstituted pyridine, pyrrole, pyrazole, imidazole, and triazole. In one aspect, a nitrogen atom in the N moiety can be bonded to X. In other aspects, N can represent other moieties not specifically recited herein, but that are described in any of the structures, figures, or examples provided herein, or that one of skill in the art would contemplate as a variant, analog, and/or suitable structure for an intended application.

In one aspect, if two or more N moieties are present in a complex and least one of the E bridging groups can be present, and can be oxygen. In another aspect, if two or more N moieties are present in a complex and all E bridging groups can be present, and can be oxygen.

In one aspect, at least one, two or three E bridging atoms can be present in the complex. For example, one, two, three, four or five E bridging atoms can be present in the complex. In one aspect, all E bridging atoms shown in the complex are present. In one aspect, at least one, two or three E bridging atoms shown in the complexes are not present. In one aspect, one, two, three or four E bridging atoms shown in the complexes are not present. In one aspect, each E bridging atom can be oxygen. In one aspect, at least two E bridging atoms are oxygen, for example, the complex can comprise two, three, four or five E bridging oxygen atoms.

In one aspect, A can be a moiety comprising 1-10 atoms, wherein the atoms are either carbon, nitrogen, oxygen or sulfur atoms. In one aspect, at least one A moiety comprises an oxygen atom bonded to X in the complex. In one aspect, both A moieties, when present, comprise an oxygen atom bonded to X in the complex. In one aspect, the A moieties can have different structures. In another aspect, the A moieties can have the same structure. In one aspect, the A moieties bonded to X forms a ring structure. For example, the ring structure can comprise 4-10 atoms, preferably 6 atoms. In one aspect, the A moieties or the linkage between the A moieties can comprise a carbon-carbon double bond. In one aspect, the A moities can be substituted with one or more groups including, but not limited to, optionally substituted alkyl, cycloalkyl, alkoxy, amino, ether, halide, hydroxy, nitro, silyl, sulfo-oxo, or thiol, as described herein.

In one aspect, the present disclosure provides a tetradentate iridium (III) complex. In another aspect, a tetradentate iridium (III) complex can be represented by the formula:

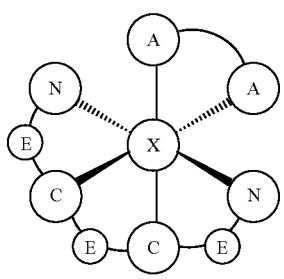

wherein X represents an iridium atom, each C represents a carbon moiety, each N represents a nitrogen moiety, each E represents an optional bridging atom, such as, for example, carbon or oxygen, and each A represents an ancillary ligand that can be used to balance the charge on the complex.

In one aspect, it should be understood that where multiple references to a ligand exist, for example, two A ligands exist in the structure above, each of the plurality of references can refer to the same or a different ligand. For example, in the structure illustrated above, each A can refer to the same or a different ancillary ligand In another aspect, a hexadentate iridium (III) complex can be represented by the formula:

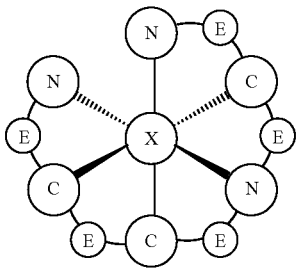

wherein X represents an iridium atom, each C represents a carbon moiety, each N represents a nitrogen moiety, each E represents an optional bridging atom, such as, for example, carbon or oxygen.

In various exemplary aspects, a tetradentate iridium (III) complex can comprise one or more of the following structures:

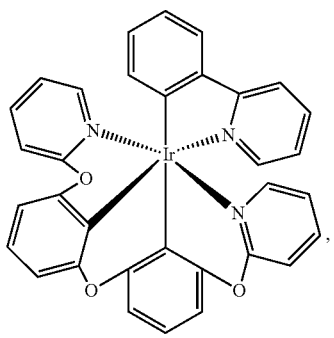

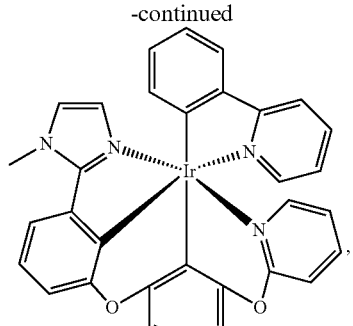

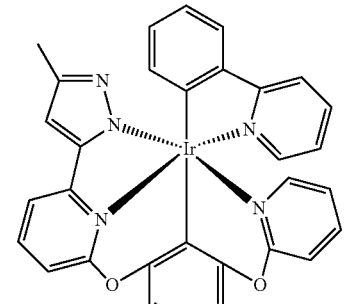

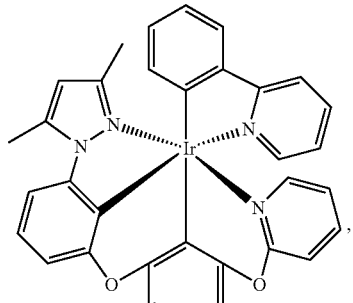

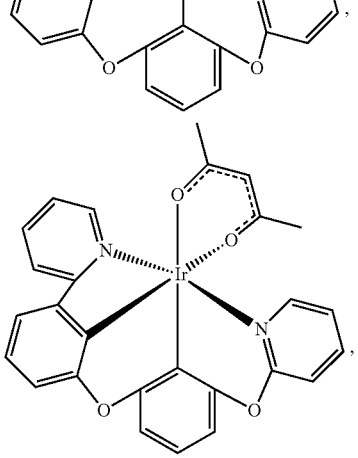

or
a combination thereof.

In one aspect, the iridium (III) complex comprises:

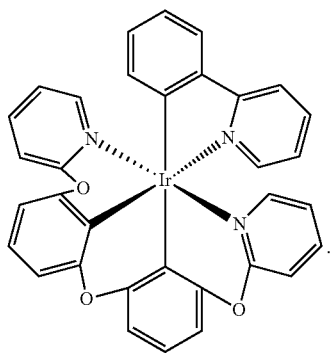

In one aspect, the iridium (III) complex comprises:

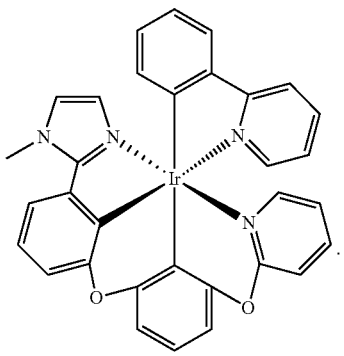

In one aspect, the iridium (III) complex comprises:

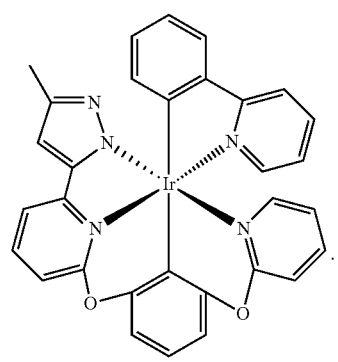

In one aspect, the iridium (III) complex comprises:

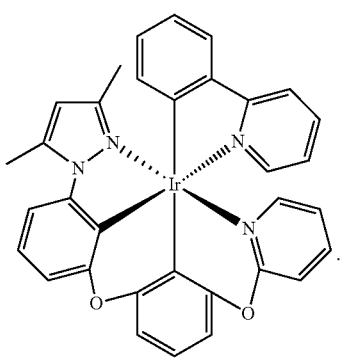

In one aspect, the iridium (III) complex comprises:

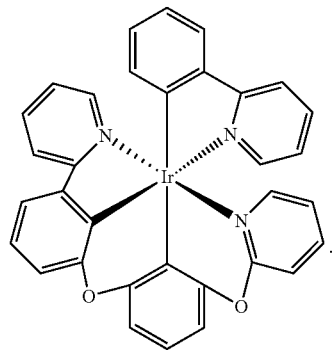

In one aspect, the iridium (III) complex comprises:

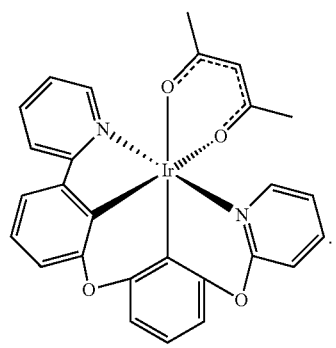

In another aspect, the inventive composition can comprise a mixture of one or more of the complexes described herein. In yet another aspect, the inventive composition can exclude, and thus, not comprise any one or more of the complexes described herein. In still other aspects, the inventive composition can comprise one or more of the complexes described herein in addition to other compounds suitable for use in a desired application.

In one aspect, the present disclosure provides a hexadentate iridium (III) complex. In another aspect, a hexadentate iridium (III) complex can be represented by the formula:

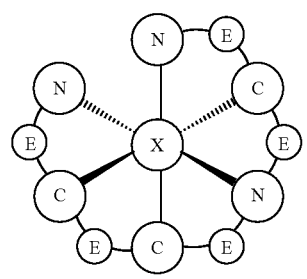

wherein X represents an iridium atom, each C represents a carbon moiety, each N represents a nitrogen moiety, each E represents an optional bridging atom, such as, for example, carbon or oxygen.

In another aspect, a hexadentate iridium (III) complex can be represented by the formula:

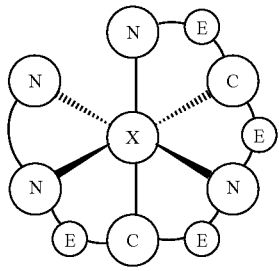

wherein X represents an iridium atom, each C represents a carbon moiety, each N represents a nitrogen moiety, each E represents an optional bridging atom, such as, for example, carbon or oxygen.

In one aspect, the iridium (III) complex comprises:

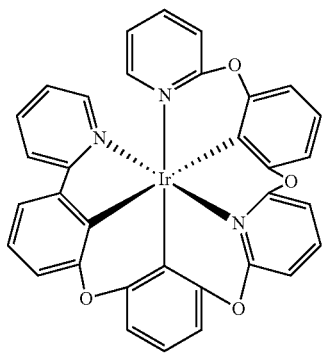

In one aspect, the iridium (III) complex comprises:

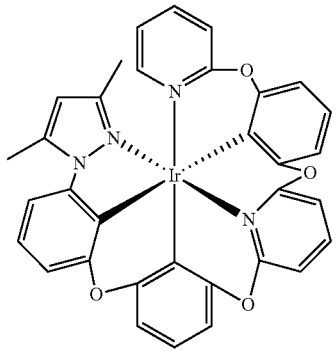

In one aspect, the iridium (III) complex comprises:

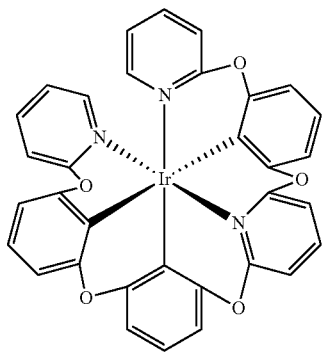

In one aspect, the iridium (III) complex comprises:

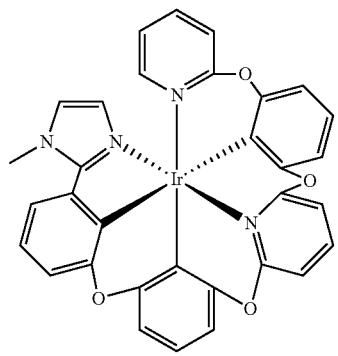

In one aspect, the iridium (III) complex comprises:

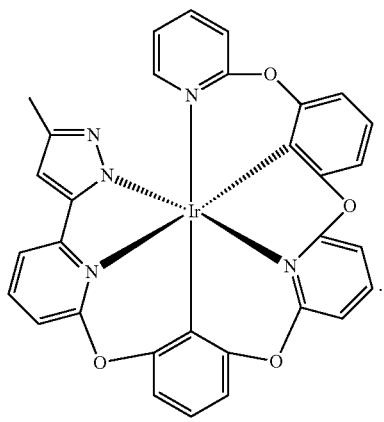

In still another aspect, the present invention provides a hexadentate iridium (III) complex represented by the formula:

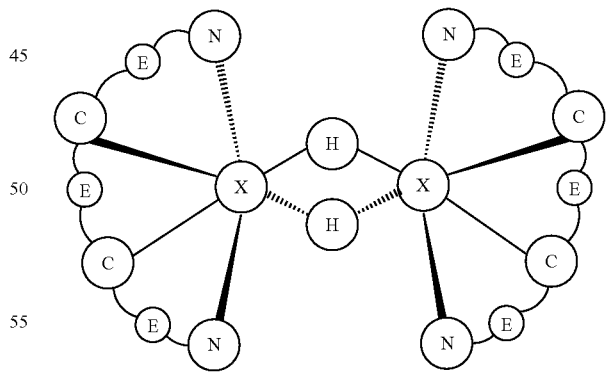

wherein X represents an iridium atom, each C represents a carbon moiety, each N represents a nitrogen moiety, each E represents an optional bridging atom, such as, for example, carbon or oxygen, and each H represent a bridging atom, such as, for example, a halogen, such as a chloride.

In one aspect, the H can be a bridging atom, such as a halogen bridging atom. The halogen can be fluoride, chloride, iodine or bromide. For example, the halogen bridging atom can be chloride.

In one aspect, the iridium (III) complex comprises:

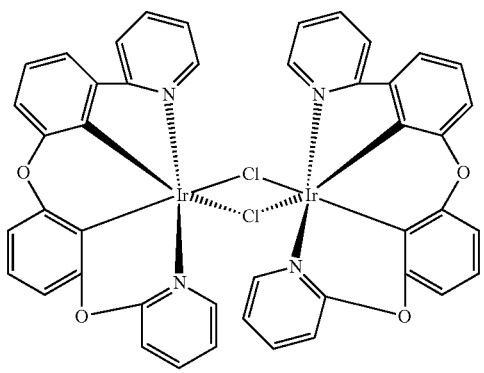

The compounds of the invention can be made using a variety of methods, including, but not limited to those recited in the examples provided herein. In other aspects, one of skill in the art, in possession of this disclosure, could readily determine an appropriate method for the preparation of an iridium complex as recited herein.

The compounds of the invention are useful in a variety of applications. As light emitting materials, the compounds can be useful in organic light emitting diodes (OLED)s, luminescent devices and displays, and other light emitting devices, or as luminescent markers in bio-applications.

The emission (and absorption) profile of the compounds can be tuned by varying the structure of the ligand surrounding the metal center. For example, compounds having a ligand with electron withdrawing substituents will generally exhibit different optical properties, including emission and absorption, than compounds having a ligand with electron donating substituents. Generally, a chemical structural change affects the electronic structure of the compound, which thereby affects the absorption and emission of the compound. Thus, the compounds of the present invention can be tailored or tuned to a specific application that desires a particular emission or absorption characteristic.

In one embodiment, the compounds can be used in an OLED. FIG. 1 shows a cross-sectional view of an OLED 100, which includes substrate 102 with an anode 104, which is typically a transparent material, such as indium tin oxide, a layer of hole-transporting material(s) (HTL) 106, a layer of light processing material 108, such as an emissive material (EML) including an emitter and a host, a layer of electron-transporting material(s) (ETL) 110, and a metal cathode layer 112.

In this embodiment, the layer of light processing material 108 can comprise one or more compounds of the present invention optionally together with a host material. The host material can be any suitable host material known in the art. The emission color of an OLED is determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. A selection of which is well within the purview of those skilled in the art.

It will be apparent that the compounds of the present invention can exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

Also disclosed herein are methods of making the iridium (III) complexes. In one aspect, the iridium (III) complexes can be made by synthetic methods described herein. Each of the complexes described herein can be produced by the methods described herein and/or can be produced by one of skill in the art, in possession of this disclosure, using methods known in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of Ir-003-acac

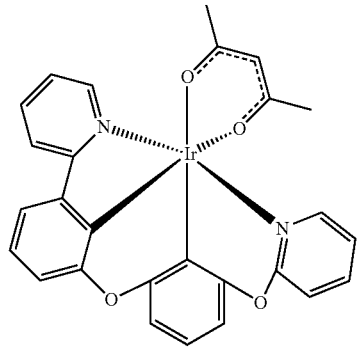

a) Synthesis of Py-O-Ph-OH

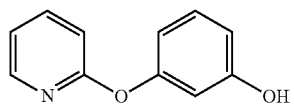 [SMILES: Oc1cccc(Oc2ccccn2)c1]

Under a nitrogen atmosphere, a pressure vessel was charged with a magnetic stir bar, resorcinol (110 mmol), 2-bromopyridine (100 mmol), 1-methylimidazole (5 mmol), and potassium carbonate (200 mmol). Pyridine (80 mL) was added and bubbled with nitrogen for 20 minutes before copper(I) iodide (10 mmol) was added and bubbled 10 minutes further. The vessel was then sealed and heated to 140° C. while stirring. After 2 days, the solution was allowed to cool. The solids were filtered off and rinsed with a 50:50 mixture of toluene and methanol. The filtrate was concentrated under reduced pressure and 150 ml of water containing 10 mL glacial acetic acid was added and shaken vigorously. The water was decanted off and 50 mL of dichloromethane (DCM) was added, forming an off white precipitate which was collected by vacuum filtration and dried with ether, resulting in the pure product Py-O-Ph-OH with a 55% yield. $^1$H NMR (CDCl$_3$): 5.98 (s, 1H), 6.59 (s, 1H), 6.62-6.69 (m, 2H), 6.94 (d, 1H), f 7.02 (dd, 1H), 7.23 (vt, 1H), 7.70 (dd, 1H), 8.23 (b, 1H).

b) Synthesis of Py-O-Ph-O-Py-Br

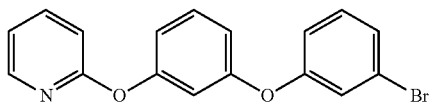 [SMILES: Brc1cccc(Oc2cccc(Oc3ccccn3)c2)c1]

Under a nitrogen atmosphere, a pressure vessel was charged with a magnetic stir bar, Py-O-Ph-OH (50 mmol), 2,6-dibromopyridine (50 mmol), 1-methylimidazole (25 mmol), and potassium carbonate (100 mmol). Toluene (80 mL) was added and bubbled with nitrogen for 20 minutes before copper(I) iodide (5 mmol) was added and the solution bubbled for 10 minutes further. The vessel was sealed and heated to 140° C. while stirring. After 2 days, the solution was allowed to cool and the solids were filtered off and rinsed with dichloromethane. The filtrate was added to a separatory funnel containing DCM and water. The water phase was washed 3 times with 75 mL DCM, and the combined organic layers were washed once with pure water. The organic layer was collected, dried with magnesium sulfate, filtered, and the filtrate concentrated under reduced pressure. The resulting oil was purified by column chromatography using DCM over silica resulting in the pure product Py-O-Ph-O-Py-Br with a 60% yield. $^1$H NMR (CDCl$_3$): 6.80-6.85 (m, 2H), 6.91 (s, 1H), 6.94 (s, 1H), 6.97-7.03 (m, 2H), 7.19 (vt, 1H), 7.21-7.24 (m, 2H), 7.36 (vt, 1H), 7.70 (dd, 1H), 8.21 (dd, 1H).

c) Synthesis of Py-O-Ph-O-Ph-Py

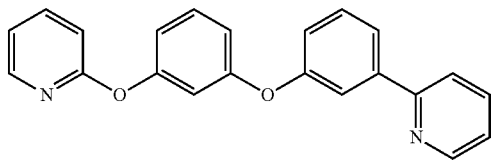 [SMILES: c1ccc(Oc2cccc(Oc3cccc(-c4ccccn4)c3)c2)nc1]

Under a nitrogen atmosphere, an oven dried three neck flask was charged with a magnetic stir bar, Py-O-Ph-O-Ph-Br (10 mmol), and 2-(tripropylstannyl)pyridine (10 mmol). Dry toluene (100 mL) was added and bubbled with nitrogen for 20 minutes before Tetrakis(triphenylphosphine)palladium(0) (0.5 mmol) was added, bubbled 10 minutes further, and brought to reflux for 2 days. After cooling, the contents of the flask were filtered, the liquid concentrated under reduced pressure, and the resulting oil was purified by column chromatography using DCM over silica to yield the pure product Py-O-Ph-O-Ph-Py with a 65% yield. $^1$H NMR (CDCl$_3$): 6.84 (vt, 1H), 6.85-6.89 (m, 2H), 6.91 (d, 1H), 6.98 (dd, 1H), 7.11 (dd, 1H), 7.24 (dd, 1H), 7.34 (vt, 1H), 7.44 (vt, 1H), 7.66-7.78 (m, 5H), 8.19 (dd, 1H), 8.67 (dd, 1H).

d) Synthesis of [(Py-O-Ph-O-Ph-Py)Ir(μ-cl)]$_2$

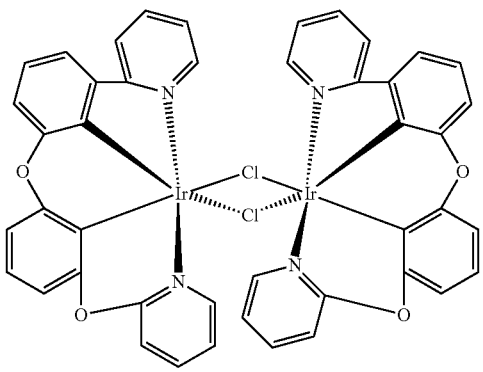

Under a nitrogen atmosphere, three neck flask was charged with a magnetic stir bar, Py-O-Ph-O-Ph-Py (10 mmol), and IrCl3.H$_2$O (10 mmol). 2-ethoxyethanol (20 mL) was added brought to 80° C. for 1 day. After cooling, the contents of the flask were concentrated under reduced pressure. DCM was added, stirred for 10 minutes, and filtered by vacuum filtration. The filtrate was collected, dried with magnesium sulfate and concentrated under reduced pressure, producing an off-white solid.

e) Synthesis of Ir-003-acac

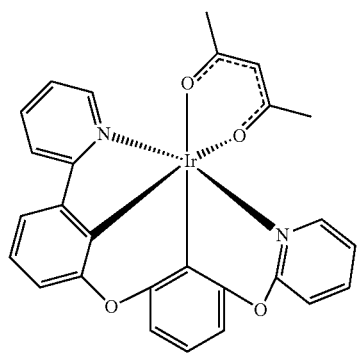

Figure 2:
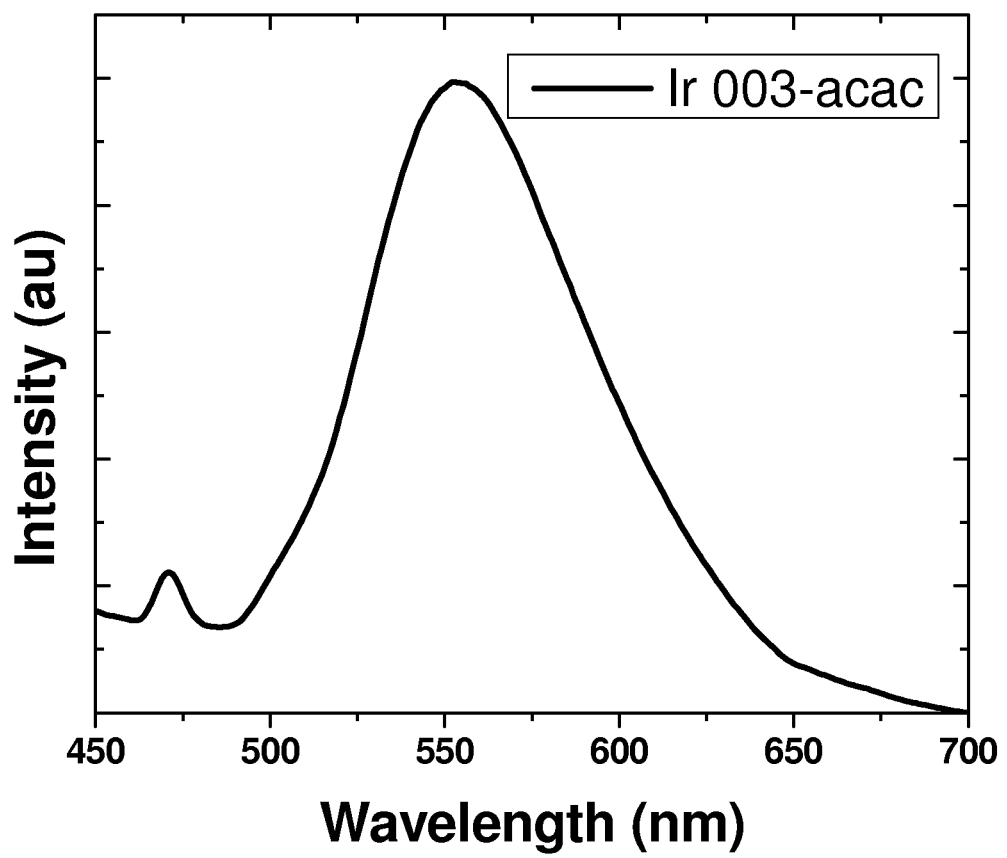
FIG. 2 illustrates the emission spectrum of an Ir003-acac complex at room temperature in dichloromethane, in accordance with various aspects of the present invention.

A round bottom flask was charged with [(Py-O-Ph-O-Ph-Py)Ir(μ-cl)]$_2$ (10 mmol), acetyl acetone (15 mmol), potassium carbonate (20 mmol), and 1,2-dichoroethane (20 mL). The mixture was stirred overnight at 80° C. After cooling the mixture was filtered, the filtrate collected, and concentrated under reduced pressure. The resulting solid was purified by column chromatography using DCM over silica to yield Ir-003-acac. FIG. 2 illustrates the emission spectrum of the prepared Ir003-acac complex, at room temperature and in dichloromethane.

What is claimed is:

1. A multidentate iridium (III) complex represented by one of the following general formulas:

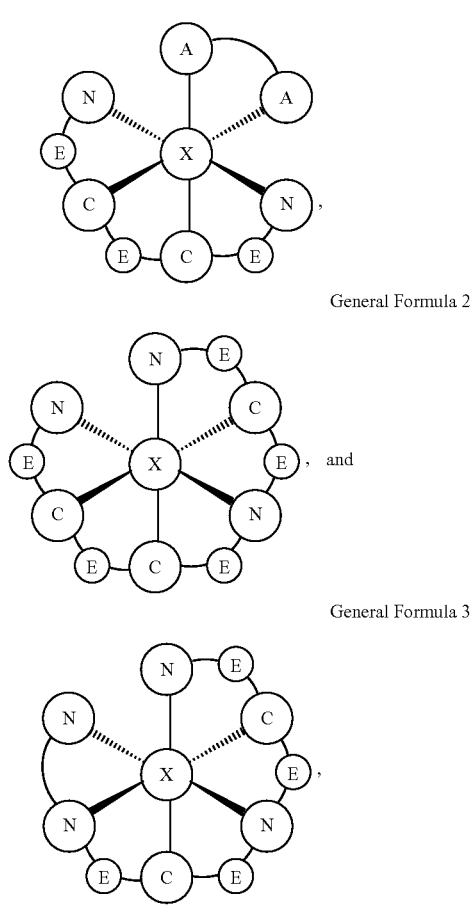

General Formula 1

General Formula 2

General Formula 3 wherein:
  X represents an iridium atom,
  each C represents a phenyl moiety,
  each N represents a pyridinyl, pyrrolyl, pyrazolyl, or imidazolyl moiety,
  each E represents a carbon atom, an oxygen atom, or a covalent bond, and at least two E represent oxygen atoms, and
  each A in General Formula 1 represents a phenyl or pyridinyl moiety, or A-A represents an acetylacetonyl moiety.

2. The multidentate iridium (III) complex of claim 1, wherein General Formula 1 is a tetradentate iridium (III) complex.

3. The multidentate iridium (III) complex of claim 2, wherein each N represents a pyridinyl or imidazolyl moiety.

4. The multidentate iridium (III) complex of claim 1, wherein General Formula 2 is a hexadentate iridium (III) complex.

5. The multidentate iridium (III) complex of claim 1, wherein General Formula 3 is a hexadentate iridium (III) complex.

6. A hexadentate iridium (III) complex represented by the formula:

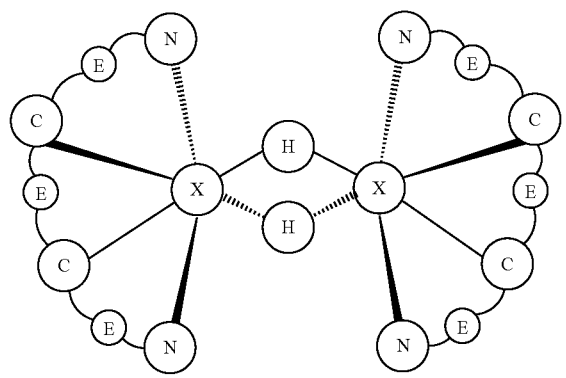

wherein:
  X represents an iridium atom,
  each C represents a phenyl moiety,
  each N represents a pyridinyl, pyrrolyl, pyrazolyl, or imidazolyl moiety,
  each E represents a carbon atom, an oxygen atom, or a covalent bond, and at least two E represent oxygen atoms, and
  each H represent a halogen bridging atom.

7. The hexadentate iridium (III) complex of claim 6, wherein each N represents a pyridinyl moiety.

8. An organic light-emitting diode (OLED) comprising one or more of the multidentate iridium (III) complexes of claim 1.

9. An organic photovoltaic device comprising, as a donor or acceptor material, one or more of the multidentate iridium (III) complexes of claim 1.

10. A luminescent bio-marker comprising one or more of the multidentate iridium (III) complexes of claim 1.

11. An iridium (III) complex having one of the following structures:

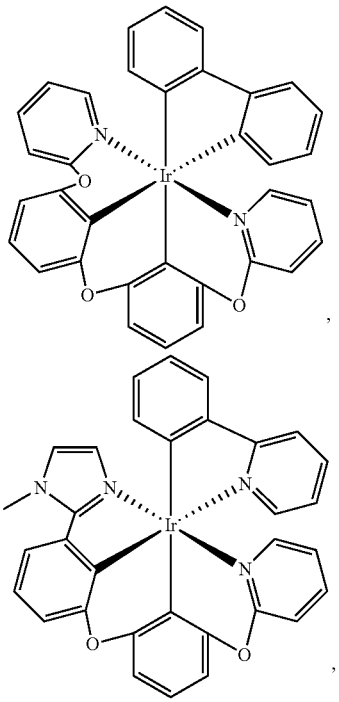

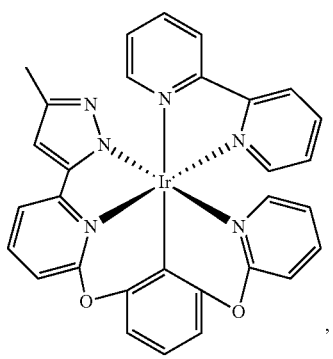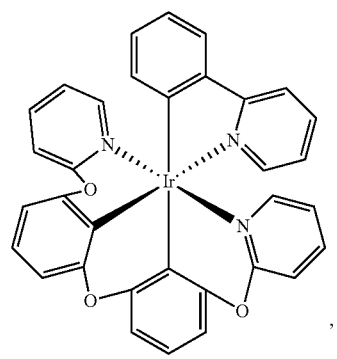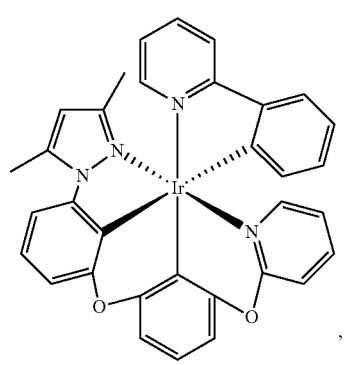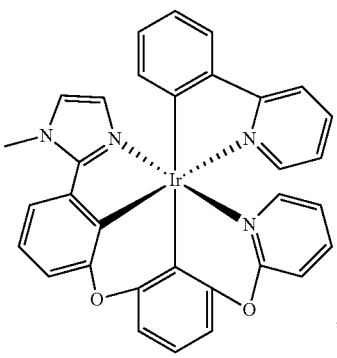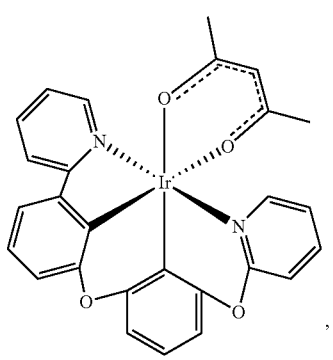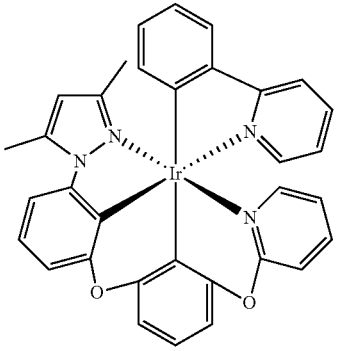

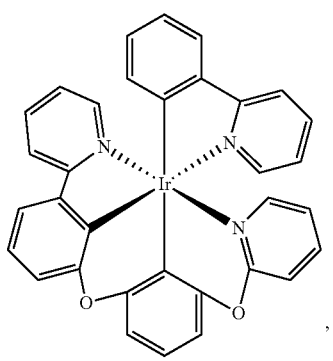
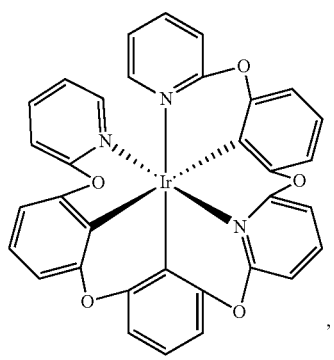
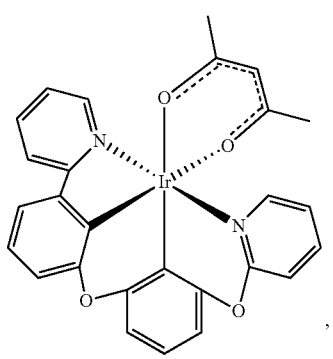
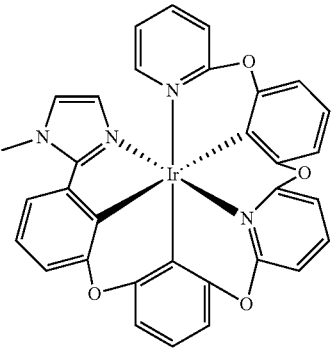
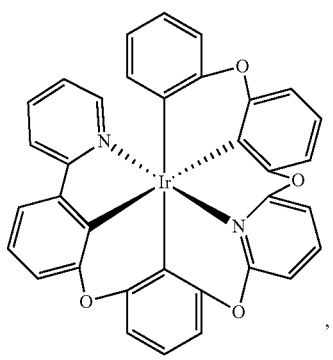
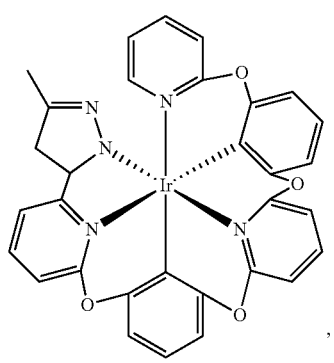
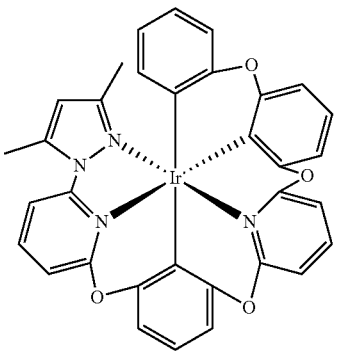
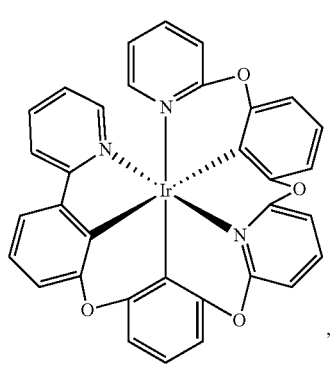

-continued

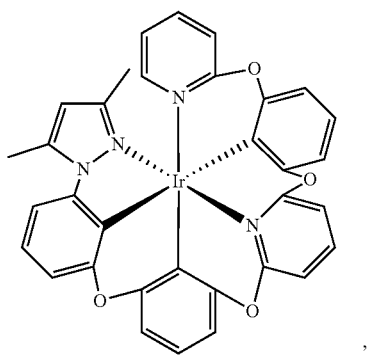

,

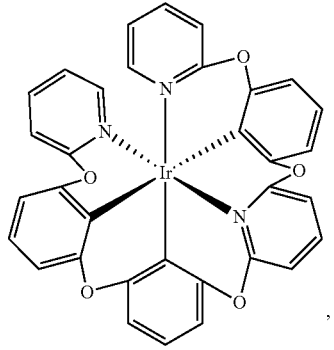

,

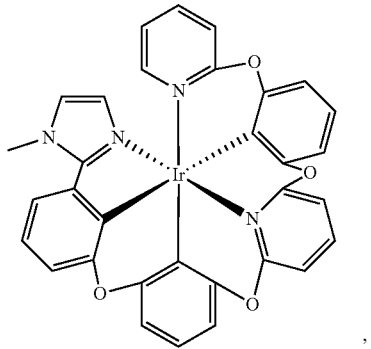

,

-continued

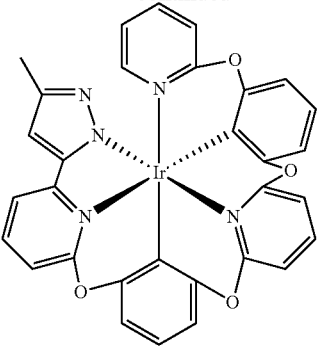

, or

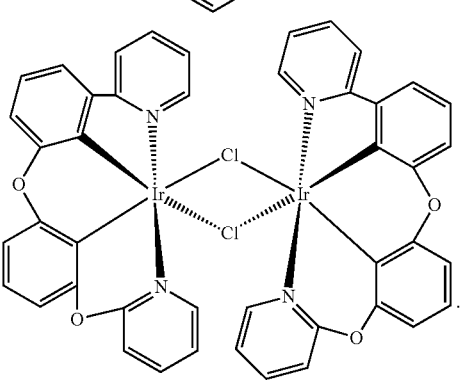

.

12. The multidentate iridium (III) complex of claim 1, wherein each E represents an oxygen atom or a covalent bond.

13. The multidentate iridium (III) complex of claim 12, wherein at least three E represent oxygen atoms.

14. The multidentate iridium (III) complex of claim 13, wherein at least four E of General Formula 2 represent oxygen atoms.

15. The multidentate iridium (III) complex of claim 1, wherein each E represents an oxygen atom.

16. The multidentate iridium (III) complex of claim 1, wherein at least three E represent oxygen atoms.

17. The multidentate iridium (III) complex of claim 1, wherein at least four E of General Formula 2 represent oxygen atoms.

* * * * *

UNITED STATES PATENT AND TRADEMARK OFFICE
CERTIFICATE OF CORRECTION

PATENT NO. : 9,221,857 B2
APPLICATION NO. : 13/446354
DATED : December 29, 2015
INVENTOR(S) : Jian Li, Eric Turner and Nathan J. Bakken Page 1 of 3

It is certified that error appears in the above-identified patent and that said Letters Patent is hereby corrected as shown below:

In the Claims

Column 18, lines 40-52, in claim 11, delete " 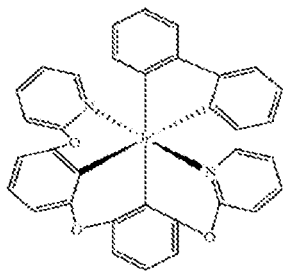 " and insert -- 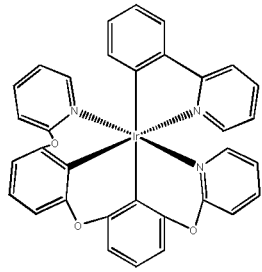 ' --.

Column 19, lines 1-15, in claim 11, delete " 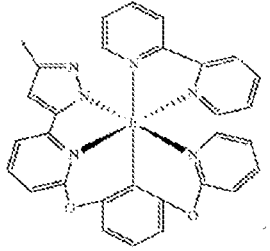 " and

Signed and Sealed this
Fifth Day of July, 2016

Michelle K. Lee
*Director of the United States Patent and Trademark Office*

CERTIFICATE OF CORRECTION (continued)
U.S. Pat. No. 9,221,857 B2

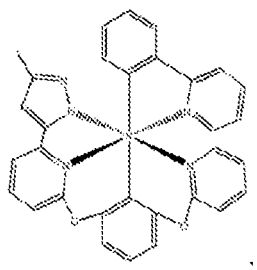

insert -- 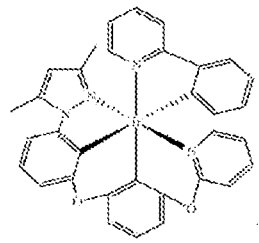 --.

Column 19, lines 20-32, in claim 11, delete " 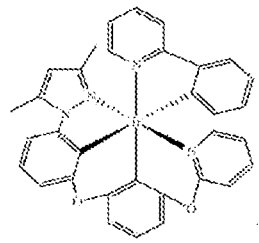 " and

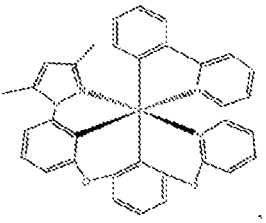

insert -- 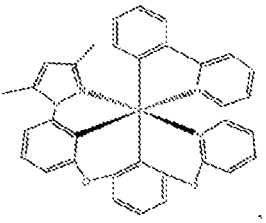 --.

Column 19, lines 36-50, in claim 11, delete " 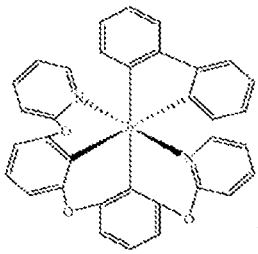 " and

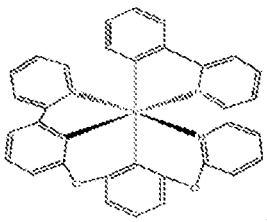

insert -- 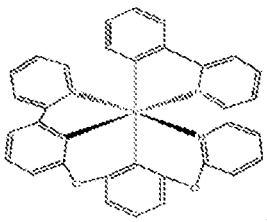 --.

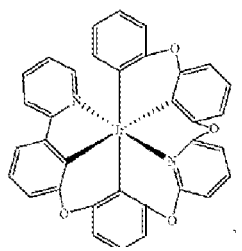

CERTIFICATE OF CORRECTION (continued)
U.S. Pat. No. 9,221,857 B2

Page 3 of 3

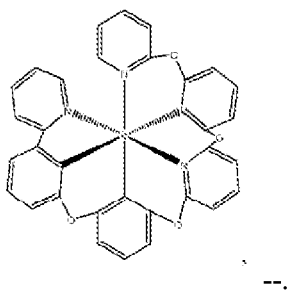

insert -- -- .

Column 21, lines 52-65, in claim 11, delete " 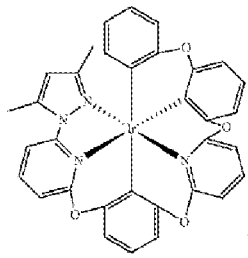 " and

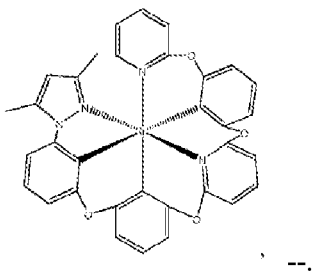

insert -- -- .

Column 24, lines 1-14, in claim 11, delete " 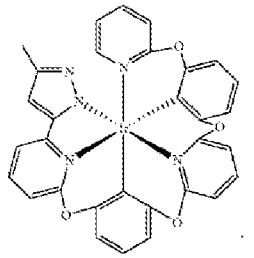 " and

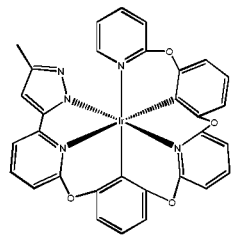

insert -- , or -- .